US010815179B1

(12) United States Patent
Boone

(10) Patent No.: US 10,815,179 B1
(45) Date of Patent: Oct. 27, 2020

(54) AROMATIC DICARBINOLS

(71) Applicant: Eastman Chemical Company, Kingsport, TN (US)

(72) Inventor: Matthew Allen Boone, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/559,887

(22) Filed: Sep. 4, 2019

(51) Int. Cl.
*C07C 43/00* (2006.01)
*C07C 41/03* (2006.01)
*C07C 43/178* (2006.01)

(52) U.S. Cl.
CPC .......... *C07C 43/1785* (2013.01); *C07C 41/03* (2013.01)

(58) Field of Classification Search
CPC ........................ C07C 43/1785; C07C 41/03
See application file for complete search history.

(56) References Cited

U.S. PATENT DOCUMENTS

| | | | |
|---|---|---|---|
| 2,578,724 | A | 12/1951 | Mertzweiller |
| 4,839,413 | A | 6/1989 | Kiehlbauch et al. |
| 4,927,876 | A | 5/1990 | Coogan et al. |
| 4,939,233 | A | 7/1990 | Jenkins et al. |
| 4,946,932 | A | 8/1990 | Jenkins |
| 5,053,556 | A | 10/1991 | Ohnishi |
| 5,137,961 | A | 8/1992 | Goos et al. |
| 5,247,040 | A | 9/1993 | Amick et al. |
| 5,296,530 | A | 3/1994 | Bors et al. |
| 5,484,849 | A | 1/1996 | Bors et al. |
| 6,451,380 | B1 | 9/2002 | Speece, Jr. et al. |
| 6,743,748 | B2 | 6/2004 | Mizuno et al. |
| 7,208,545 | B1 | 4/2007 | Brunner et al. |
| 9,932,486 | B1 | 4/2018 | Cogar et al. |
| 2009/0035696 | A1 | 2/2009 | Matsuoka |
| 2009/0076311 | A1 | 3/2009 | Sato et al. |
| 2012/0289721 | A1 | 11/2012 | End et al. |
| 2015/0239816 | A1 | 8/2015 | Zaragoza Doerwald et al. |

FOREIGN PATENT DOCUMENTS

| EP | 0 492 847 A2 | 7/1992 |
|---|---|---|
| WO | WO 2007/094922 A2 | 8/2007 |

OTHER PUBLICATIONS

USPTO Office Action dated Apr. 30, 2020 recieved in co-pending U.S. Appl. No. 16/560,161.
Trost et al.; "Model for Asymmetric Induction in the Diels-Alder Reaction;" Journal of the American Chemical Society; vol. 102; 1980; pp. 7595-7596.
USPTO Office Action dated Apr. 6, 2020 received in co-pending U.S. Appl. No. 16/559,842.
USPTO Notice of Allowance dated Nov. 1, 2019 received in co-pending U.S. Appl. No. 16/559,977.
USPTO Notice of Allowance dated Dec. 10, 2019 received in co-pending U.S. Appl. No. 16/559,977.
USPTO Notice of Allowance dated Nov. 1, 2019 received in co-pending U.S. Appl. No. 16/559,988.
USPTO Notice of Allowance dated Dec. 11, 2019 received in co-pending U.S. Appl. No. 16/559,988.
Kluge et al.; "Phosphonate Reagents for the Synthesis of Enol Ethers and One-Carbon Homologation to Aldehydes;" J. Org. Chem.; vol. 44; No. 26; 1979; pp. 4847-4852.
Co-pending U.S. Appl. No. 16/559,842, filed Sep. 4, 2019; Boone.
Co-pending U.S. Appl. No. 16/559,871, filed Sep. 4, 2019; Boone.
Co-pending U.S. Appl. No. 16/559,912, filed Sep. 4, 2019; Boone.
Co-pending U.S. Appl. No. 16/559,897, filed Sep. 4, 2019; Boone.
Co-pending U.S. Appl. No. 16/559,880, filed Sep. 4, 2019; Boone et al.
Co-pending U.S. Appl. No. 16/559,859, filed Sep. 4, 2019; Boone et al.
Co-pending U.S. Appl. No. 16/560,146, filed Sep. 4, 2019; Boone et al.
Co-pending U.S. Appl. No. 16/560,161, filed Sep. 4, 2019; Boone et al.
Co-pending U.S. Appl. No. 16/559,977, filed Sep. 4, 2019; Boone.
Co-pending U.S. Appl. No. 16/559,988, filed Sep. 4, 2019; Boone et al.
ASTM D1544; Standard Test Method for Color of Transparent Liquids (Gardner Color Scale).
ASTM D2354-10$^{e1}$; Standard Test Method for Minimum Film Formation Temperature (MFFT) of Emulsion Vehicles.
ASTM D4946; Standard Test Method for Blocking Resistance of Architectural Paints.
ASTM D6886; Standard Test Method for Determination of the Weight Percent Individual Volatile Organic Compounds in Waterborne Air-Dry Coatings by Gas Chromatography.
Burczyk, B. et al.; "Relations between chemical structure and surface activity I: Synthesis and properties of aqueous solutions of acetals formed from aliphatic aldehydes and monoalkyl ethers of ethylene glycols;" Tenside Detergents; 15(2); 1978; pp. 68-71.
Burczyk, B. et al.; "Surface Properties of Selected Linear and Cyclic Acetals;" Tensioactivos: Biodegradabilidad, Fis.-Quim. Apl., Jorn. Com. Esp. Deterg.; 11$^{th}$; 1980; pp. 581-601.
Cohen, R. et al.; "Foam stabilizing properties of linear acetals containing oxyethylene units in their molecules;" Tenside Detergents; 18 (4); 1981; pp. 202-205.
Duchene, A. et al.; "Alxoxyméthyltributylétains précurseurs d'alcoxyméthyllithiums : application à la synthèse de monoéthers d'α-glycols et à l'homologation de cétones en aldéhydes;" Bulletin De La Societe Chimique De France; 1985; No. 5; pp. 787-792.
Getzkin, AJ. et al.; "Synthesis of Some Symmetrical Aldehyde Glycol Monoether Acetals;" Journal of the American Pharmaceutical Association, Scientific Edition; 49; 1960; pp. 746-750.
Kanno, T. et al.; "Oxygenation of Aromatic Vinyl Ethers. A Noticeable Formation of Epoxides and Reaction Mechanism;" Bull. Chem. Soc. Jpn.; 54; 1981; pp. 2330-2336.

(Continued)

*Primary Examiner* — Sikarl A Witherspoon
(74) *Attorney, Agent, or Firm* — Matthew W. Smith

(57) ABSTRACT

Disclosed are aromatic dicarbinol compounds that may have utility in a variety of chemical applications such as plasticizers, diluents, wetting agents and paint additives and as intermediates in chemical processes. The aromatic dicarbinols have particular utility as reactants in processes for the synthesis of aromatic enol ether compounds.

6 Claims, No Drawings

(56) References Cited

OTHER PUBLICATIONS

Moszner, N. et al.; "Reaction behavior of monomeric β-ketoesters. 2. Synthesis, characterization and polymerization of methacrylate group containing enamines;" Polymer Bulletin; 32; pp. 419-426; (1994).
Presidential Green Chemistry Challenge: 2005 Designing Greener Chemical Award; Archer Daniels Midland Company; Archer RC™: A Nonvolatile, Reactive Coalescent for the Reduction of VOCs in Latex Paints; United States Environmental Protection Agency; Accessed via the web on Jun. 6, 2018; https://www.epa.gov/greenchemistry/presidential-green-chemistry-challenge-2005-designing-greener-chemicals-award.
Robinson, M. et al.; "Epoxide ring-opening and Meinwald rearrangement reactions of epoxides catalyzed by mesoporous aluminosilicates;" Organic & Biomolecular Chemistry; 2009; 7; pp. 2559-2564.
Safa, K. et al.; "1,4-bis[2,2-bis(trimethylsilyl)ethenyl]benzene: Regioselective ring opening of its a,B-eposybix(silane) with some nucleophiles;" Journal of Organometallic Chemistry; 694; 20019; pp. 1907-1911.
Smith, O.W. et al.; "New vinyl ester monomers for emulsion polymers;" Progress in Organic Coatings; 22; 1993; pp. 19-25.
Sokolowski, A. et al.; "Acetals and Ethers. Part IV. Synthesis of Acetals from Aliphatic Aldehydes and Monoalkyl Ether of Ethylene Glycols;" Polish Journal of Chemistry (formerly Roczniki Chemii); 53(4); 1979; pp. 905-912.
Sokolowski, A. et al.; "Statistical Evaluation of the Influence of Linear Acetal Structures on Their Adsorption at the Aqueous Solution-Air Interface;" Comunicaciones presentadas a las XII Jornadas del Comite Espanol de la Detergencia; Asociacion De Investigacion De Detergentes, Tens; 1981; pp. 491-507.

AROMATIC DICARBINOLS

FIELD OF THE INVENTION

This application relates to chemistry generally. In particular, this application relates dicarbinols and more particularly to aromatic dicarbinols.

BACKGROUND OF THE INVENTION

Dicarbinols are useful in a variety of chemical applications such as plasticizers, diluents, wetting agents and paint additives and as intermediates in chemical processes. Diluents, wetting agents and paint additives often are volatile and evaporate into the atmosphere during use. For example, coalescing aids that are added to water-based paints, act as temporary plasticizers in latex emulsions. The coalescing aids lower the glass transition temperature (Tg) of the latex polymer and as the paint dries, the polymers that have been softened by the coalescing aid are allowed to flow together and form a film after the water has left the system. Coalescing aids that are volatile evaporate out of the film. This allows the polymer to return to the original Tg thereby giving harder films for better block and print resistant coatings.

Due to environmental concerns, the use of volatile materials such as paint additives, plasticizers, diluents, wetting agents and coalescing aids are increasing undesirable. There is a need for materials that can be used as paint additives, plasticizers, diluents, wetting agents and coalescing aids that exhibit low volatility. There is also a need for materials that can be used to make paint additives, plasticizers, diluents, wetting agents and coalescing aids that have low volatility.

SUMMARY OF THE INVENTION

The Invention is set forth in the appended claims.

The present relates to an aromatic dicarbinol compound according to Formula I:

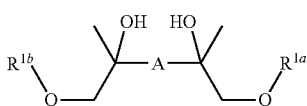

I wherein: A is $(C_{8-20})$ aryl;
$R^{1a}$ and $R^{1b}$ are independently

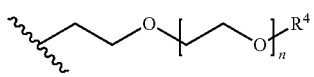

or

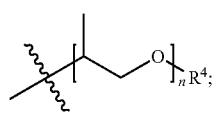

each $R^4$ is independently $(C_{1-12})$alkyl, or $—C(O)R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;

each $R^6$ is $(C_{1-4})$alkoxy, or oxo; and
each n is independently an integer from 1 to 15.

DETAILED DESCRIPTION

Definitions

In this specification and in the claims that follow, reference will be made to a number of terms, which shall be defined to have the following meanings.

"Alkyl" means an aliphatic hydrocarbon. The alkyl can specify the number of carbon atoms, for example $(C_{1-5})$ alkyl. Unless otherwise specified, the alkyl group can be unbranched or branched. In some embodiments, the alkyl group is branched. In some embodiments, the alkyl group is unbranched. Non-limiting examples of alkanes include methane, ethane, propane, isopropyl (i.e., branched propyl), butyl, and the like.

"Alkenyl" means an aliphatic hydrocarbon with one or more unsaturated carbon-carbon bonds. The alkenyl can specify the number of carbon atoms, for example $(C_{2-12})$ alkenyl. Unless otherwise specified, the alkyl group can be unbranched or branched. In some embodiments, the alkyl group is branched. In some embodiments, the alkyl group is unbranched. Non-limiting examples of alkanes include ethenyl, propenyl, butenyl, hexa-3,5-dienyl, and the like.

"Alcohol" means a chemical containing one or more hydroxyl groups.

"Aldehyde" means a chemical containing one or more —C(O)H groups.

"Cycloalkyl" means a cyclic hydrocarbon compound. The cycloalkyl can specify the number of carbon atoms in ring system, for example $(C_{3-8})$cycloalkyl. Non-limiting examples of cycloalkyl include cyclopropyl, cyclobutyl, cyclohexyl, and cyclooctyl.

"Aryl" means a ring system made up carbon atoms that has at least one ring that is aromatic. The carbon units making up the aryl ring may be specified, for example 5- to 9-membered aryl. Non-limiting examples of aryl include phenyl, naphthyl, 2,3-dihydro-1H-indene, and 1,2,3,4-tetrahydronaphthalene.

Values may be expressed as "about" or "approximately" a given number. Similarly, ranges may be expressed herein as from "about" one particular value and/or to "about" or another particular value. When such a range is expressed, another aspect includes from the one particular value and/or to the other particular value. Similarly, when values are expressed as approximations, by use of the antecedent "about," it will be understood that the particular value forms another aspect.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

"Chosen from" as used herein can be used with "or" or "and." For example, Y is chosen from A, B, and C means Y can be individually A, B, or C. Alternatively, Y is chosen from A, B, or C means Y can be individually A, B, or C; or a combination of A and B, A and C, B and C, or A, B, and C.

Presented herein are compounds which can be used to make enol ethers which have can be used as diluents, wetting agents, coalescing aids and paint additives.

In some embodiments the invention is a compound according to Formula I:

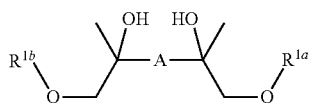

I wherein: A is $(C_{8-20})$ aryl;
$R^{1a}$ and $R^{1b}$ are independently

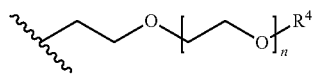

or

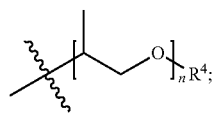

each $R^4$ is independently $(C_{1-12})$alkyl, or —C(O)$R^5$;
each $R^5$ is $(C_{1-12})$alkyl unsubstituted or substituted by $R^6$, $(C_{2-12})$alkenyl unsubstituted or substituted by $R^6$, $(C_{3-8})$cycloalkyl, or 5- to 9-membered aryl;
each $R^6$ is $(C_{1-4})$alkoxy, or oxo; and
each n is independently an integer from 1 to 15.

In some embodiments, A is 1,2-, 1,3-, or 1,4-disubstituted phenyl. In some embodiments, each n is an integer from 1 to 3.

In some embodiments each $R^4$ is hydrogen. In some embodiments, each $R^4$ is $(C_{1-12})$alkyl. In some embodiments, each $R^4$ is independently ethyl. In some embodiments, each $R^4$ is $(C_{2-12})$alkenyl. In some embodiments, each $R^4$ is —C(O)$R^5$.

In some embodiments of, each $R^5$ is $(C_{1-12})$alkyl unsubstituted or substituted by $R^6$. In some embodiments, each $R^5$ is $(C_{1-12})$alkenyl unsubstituted or substituted by $R^6$. In some embodiments, each $R^5$ is $(C_{3-8})$cycloalkyl. In some embodiments, each $R^5$ is 5- to 9-membered aryl.

In some embodiments each n is an integer from 1 to 2. In some embodiments, each n is an integer from 1 to 3. In some embodiments, each n is an integer from 1 to 4. In some embodiments, each n is an integer from 1 to 5. In some embodiments, n is an integer from 1 to 6. In some embodiments, n is an integer from 1 to 7. In some embodiments, n is an integer from 1 to 8. In some embodiments, n is an integer from 1 to 9. In some embodiments, n is an integer from 1 to 10. In some embodiments, n is an integer from 1 to 11. In some embodiments, n is an integer from 1 to 12. In some embodiments, n is an integer from 1 to 13. In some embodiments, n is an integer from 1 to 14. In some embodiments, n is an integer from 1 to 15.

In some embodiments, the compounds of Formulas I have a volatile organic content of less than 50 wt % according to ASTM D6886. In some embodiments, the volatile organic content is less than 30 wt %. In some embodiments, the volatile organic content is less than 10 wt %. In some embodiments, the volatile organic content is less than 5 wt %. In some embodiments, the volatile organic content is less than 3 wt %. In some embodiments, the volatile organic content is less than 2 wt %. In some embodiments, the volatile organic content is less than 1 wt %. In some embodiments, the volatile organic content is less than 0.8 wt %.

Compositions

Disclosed are aromatic dicarbinol compounds that have particular utility as reactants in processes for the synthesis of aromatic enol ether compounds.

In some embodiments, the composition comprises the dicarbinol compounds represented by Formulas I. In some embodiments, the compounds of Formula I are aromatic dicarbinols represented by Formulas 1-16:

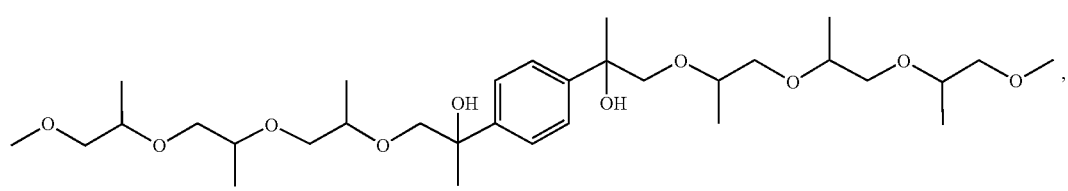

1

2

-continued
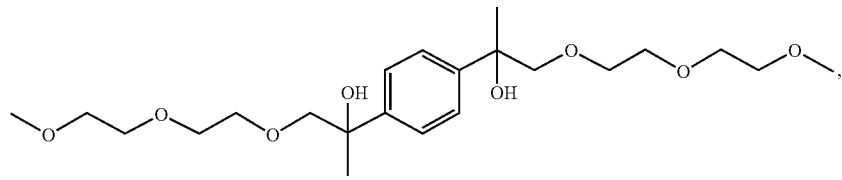
3
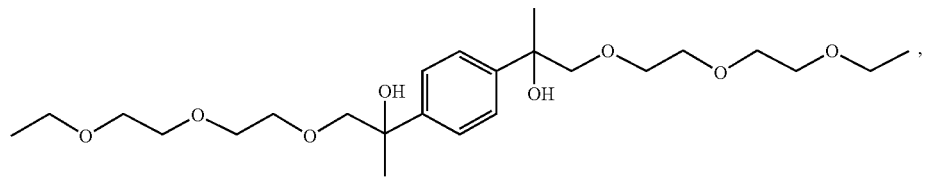
4
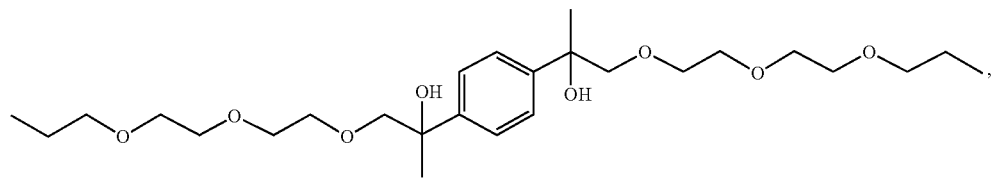
5
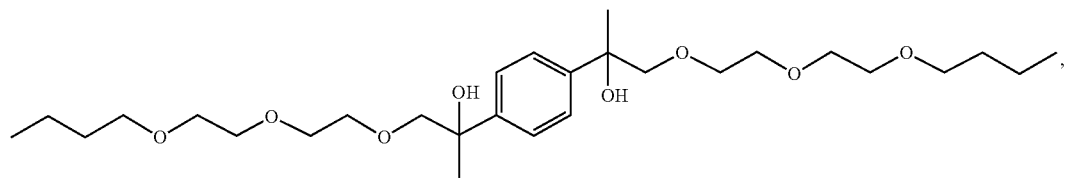
6
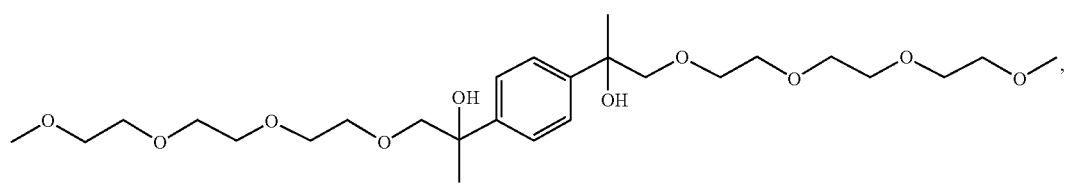
7
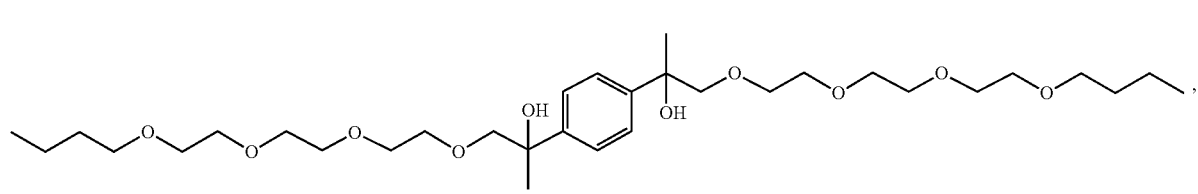
8
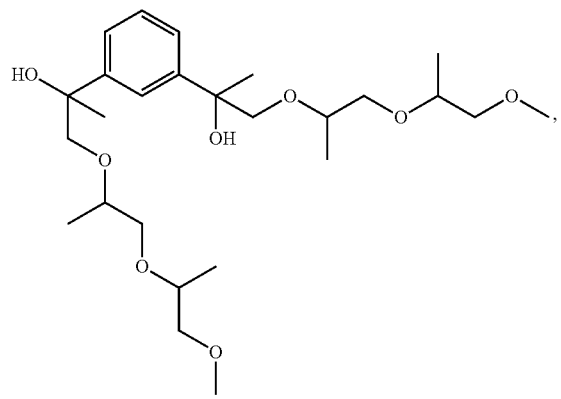
9

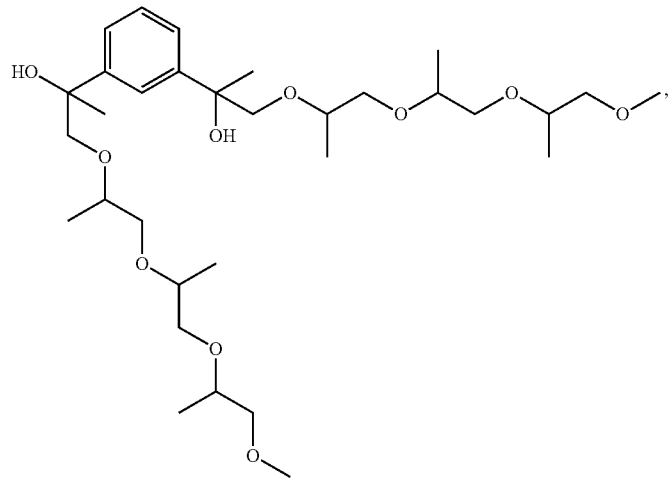
10
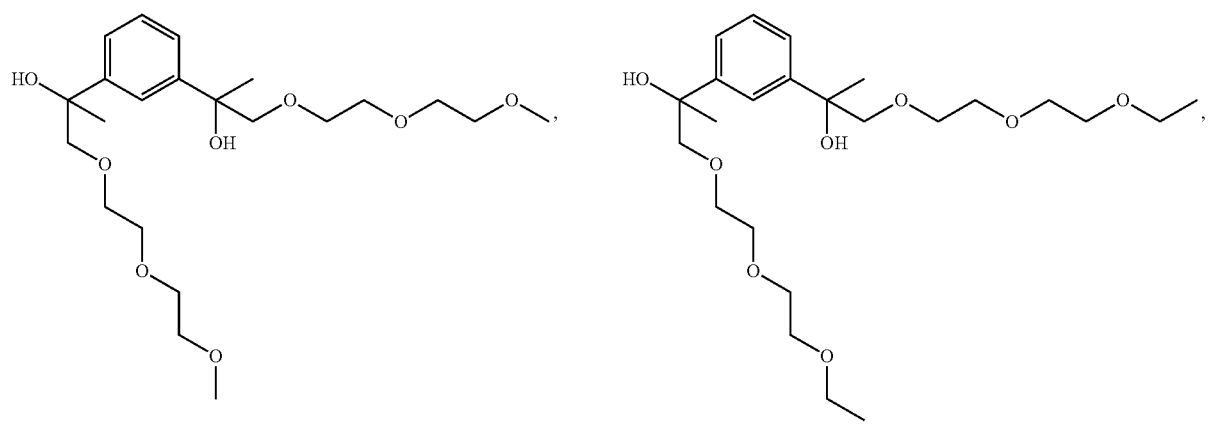
11
12
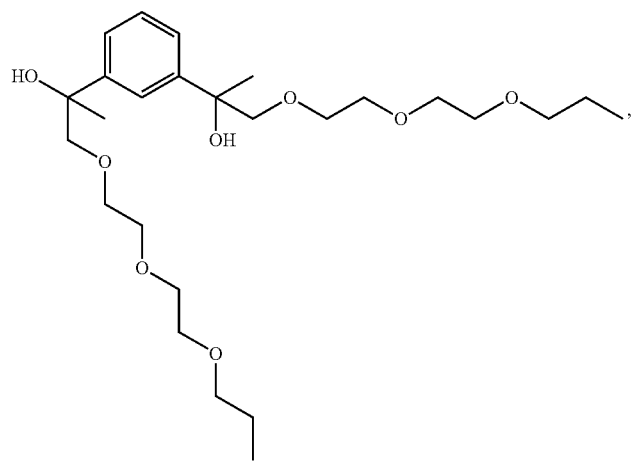
13

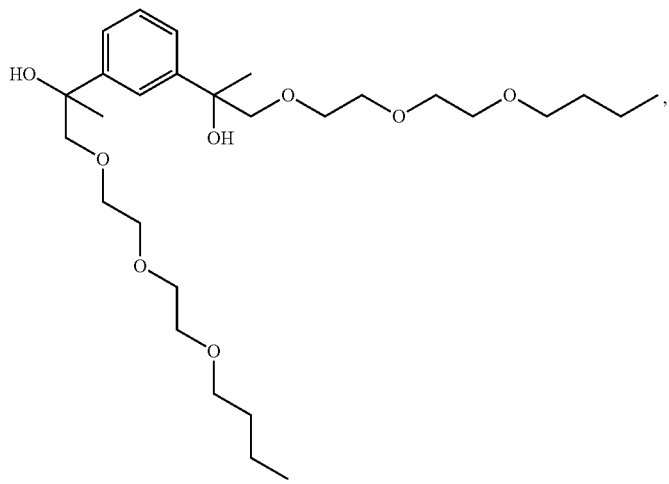

14

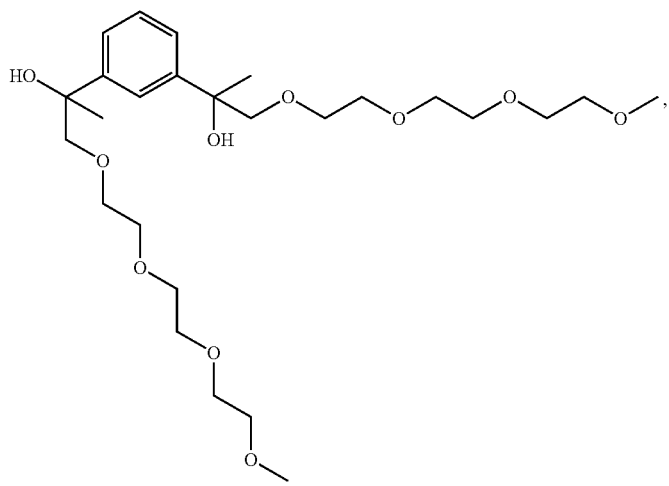

15

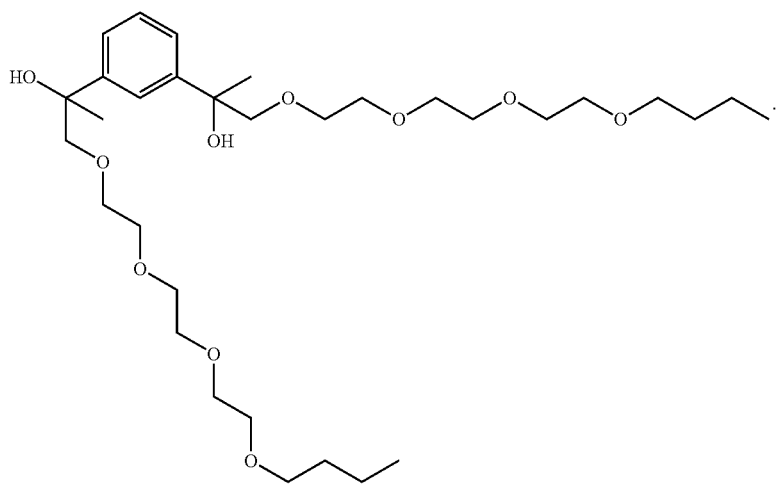

16

The aromatic dicarbinol compounds depicted by Formulas 1-16 are representative of the aromatic dicarbinol compounds claimed herein. Isomers of the aromatic dicarbinol compounds depicted by Formulas 1-16 are expected to be produced during synthesis of the aromatic dicarbinol compounds depicted by Formulas 1-16. All isomers of the aromatic dicarbinol compounds depicted by Formulas 1-16 and are within the scope of the claims set forth herein.

The aromatic dicarbinol compounds of the of the present invention include those having a weight percent volatile content of less than 50%, as measured according to ASTM Method D6886. This test may be conducted generally by heating the sample in a forced air oven at 110° C. for 60 minutes. The weight loss after the test is deemed to result from a loss of volatiles originally present in the sample; the percent volatile present in the original sample may then be calculated. Although the cited test can be conducted on coating compositions containing other components such as latex polymers, the values cited herein may be obtained from a sample of the additive itself. Thus, the weight percent volatile of a film-hardening aid may be used herein as a yardstick to measure the amount of VOC the additive would contribute to the VOC in a particular end use such as a component of a coating composition.

EXAMPLES

This invention can be further illustrated by the following examples thereof, although it will be understood that these examples are included merely for purposes of illustration and are not intended to limit the scope of the invention unless otherwise specifically indicated.

Abbreviations mL is milliliter; wt % is weight percent; eq is equivalent(s); hrs or h is hour(s); mm is millimeter; m is meter; GC is gas chromatography; ° C. is degree Celsius; min is minute; $t_R$ is retention time; VOC is volatile organic compound; MeP is methyl palmitate; w/v is weight/volume; μL is microliter. RFHA is reactive film-hardening additive.

General Procedure for Epoxide Opening

To a 4-necked round-bottom flask fitted with thermocouple, nitrogen inlet, and overhead stirrer was added glycol ether (5 equiv.). Then the di-epoxide was added all at once. The mixture was heated to an internal temperature of 50° C. (note: the 1,4-di-epoxide is a solid that requires some additional time for dissolution; the 1,3-di-epoxide is a liquid at room temperature). The KOH (90%, flakes, 2 equiv.) was added portion-wise such that the internal temperature did not exceed 70° C. (usually over the course of 1 to 1.5 hrs). Once the addition of base was complete, the reaction was monitored by 1H NMR (aliquot was dissolved in DMSO-d6). After the di-epoxide was completely consumed, the mixture was cooled to room temperature. The mixture was then poured into ice water. Toluene was added to the mixture and then acetic acid (2.05 equiv. was added). The mixture was transferred to a separatory funnel. After layer separation, the aqueous layer was back-extracted with ethyl acetate. The organics were combined and dried with $MgSO_4$, while stirring with activated carbon. The mixture was filtered, and the volatiles were removed using a rotary evaporator. Kugelrohr distillation was used to remove excess glycol ether, if needed.

Example 1: Preparation of 2,2'-(1,4-phenylene)bis (1-((1-((1-methoxypropan-2-yl)oxy)propan-2-yl) oxy)propan-2-ol) [1]

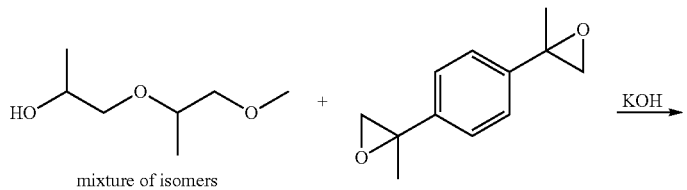

mixture of isomers

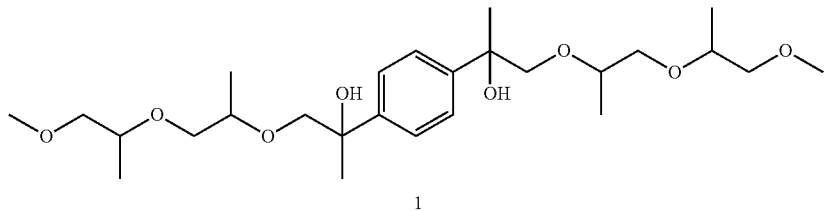

1

LC-MS $t_R$: 6.46 min (Exact mass: 486.32 m/z, found: 486.3 m/z).

Example 2: Preparation of 13,13'-(1,4-phenylene) bis(4,7,10-trimethyl-2,5,8,11-tetraoxatetradecan-13-ol) [2]

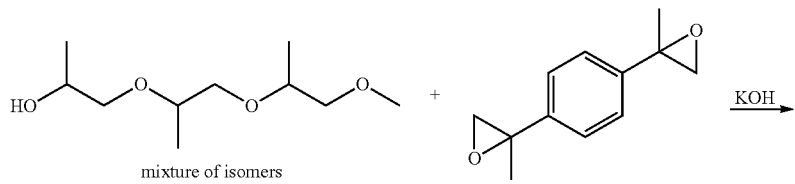

mixture of isomers

-continued
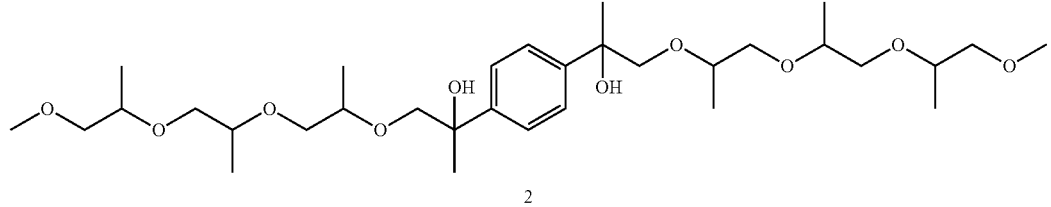
2
LC-MS $t_R$: 7.54 min (Exact mass: 602.40 m/z, found: 602.4 m/z).
Example 3: Preparation of 2,2'-(1,4-phenylene)bis (1-(2-(2-methoxyethoxy)ethoxy)propan-2-ol) [3]
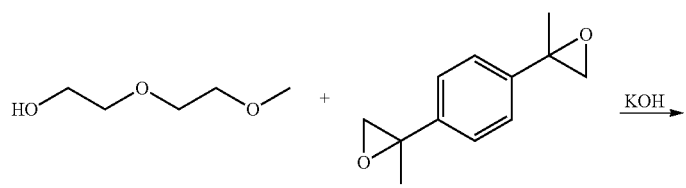
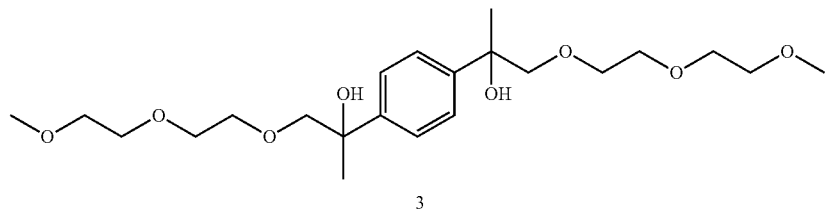
3
LC-MS $t_R$: 4.44 min (Exact mass: 430.26 m/z, found: 430.3 m/z).
Example 4: Preparation of 2,2'-(1,4-phenylene)bis (1-(2-(2-ethoxyethoxy)ethoxy)propan-2-ol) [4]
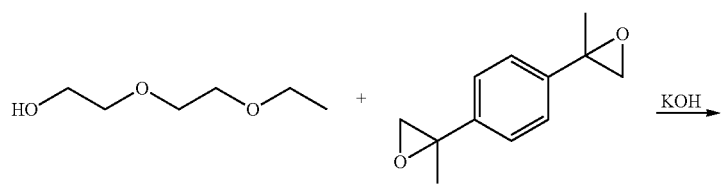
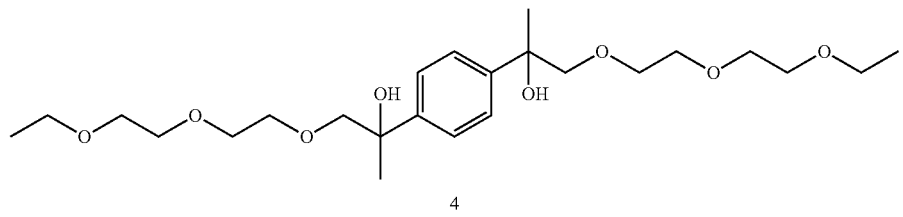
4

LC-MS $t_R$: 5.32 min (Exact mass: 458.29 m/z, found: 458.3 m/z).
Example 5: Preparation of 2,2'-(1,4-phenylene)bis (1-(2-(2-propoxyethoxy)ethoxy)propan-2-ol) [5]
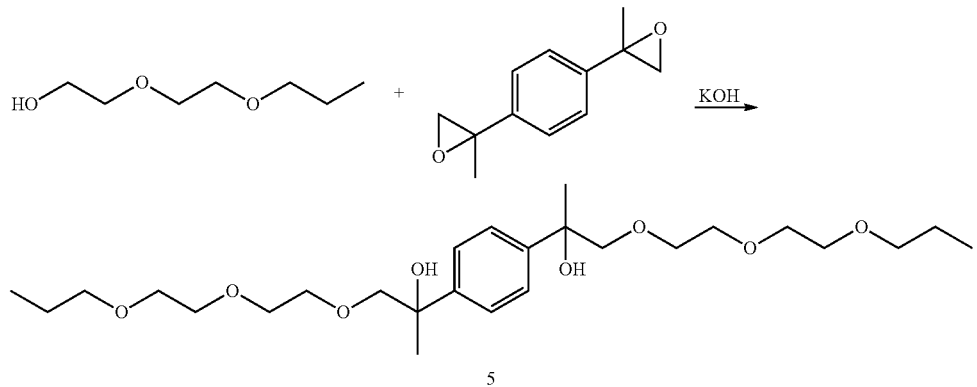
LC-MS $t_R$: 6.46 min (Exact mass: 486.32 m/z, found: 486.3 m/z).
Example 6: Preparation of 2,2'-(1,4-phenylene)bis (1-(2-(2-butoxyethoxy)ethoxy)propan-2-ol) [6]
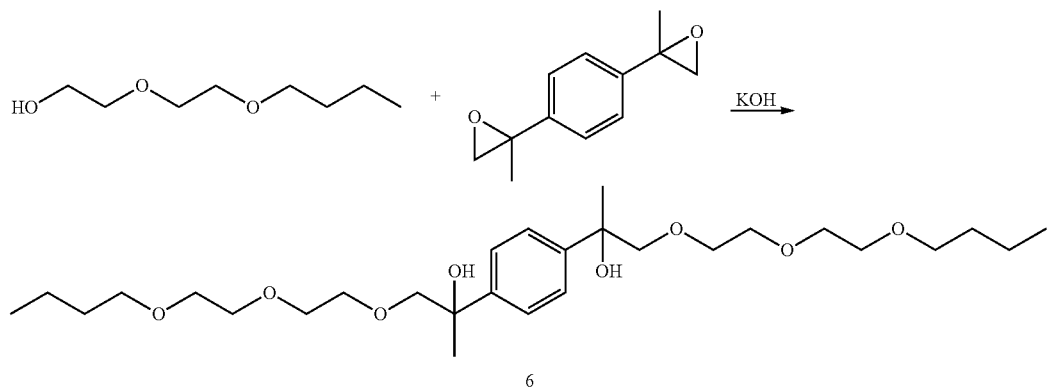
LC-MS $t_R$: 7.60 min (Exact mass: 514.35 m/z, found: 514.4 m/z).
Example 7: Preparation of 13,13'-(1,4-phenylene) bis(2,5,8,11-tetraoxatetradecan-13-ol) [7]
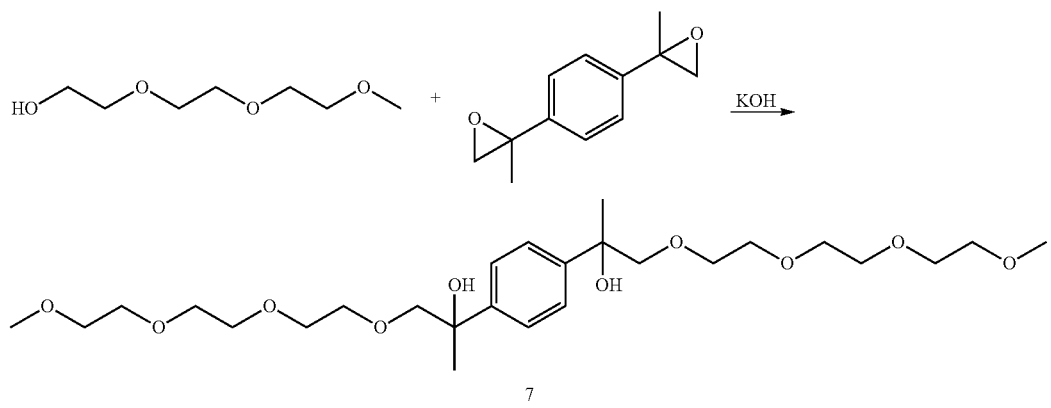

LC-MS $t_R$: 4.62 min (Exact mass: 518.31 m/z, found: 518.3 m/z).

Example 8: Preparation of 2,2'-(1,4-phenylene)bis(4,7,10,13-tetraoxaheptadecan-2-ol) [8]

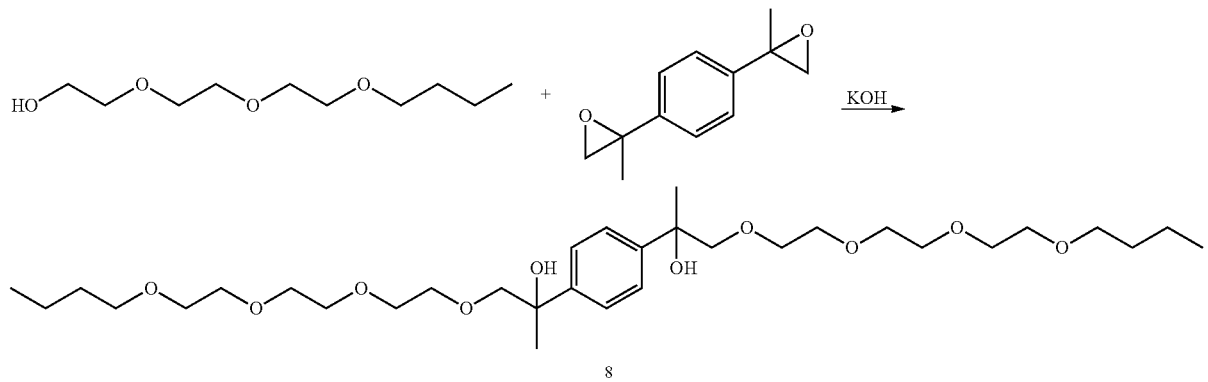

LC-MS $t_R$: 7.54 min (Exact mass: 602.40 m/z, found: 602.4 m/z).

Example 9: Preparation of 2,2'-(1,3-phenylene)bis(1-((1-((1-methoxypropan-2-yl)oxy)propan-2-yl)oxy)propan-2-ol) [9]

Example 10: Preparation of 2,2'-(1,3-phenylene)bis(1-((1-((1-methoxypropan-2-yl)oxy)propan-2-yl)oxy)propan-2-ol) [10]

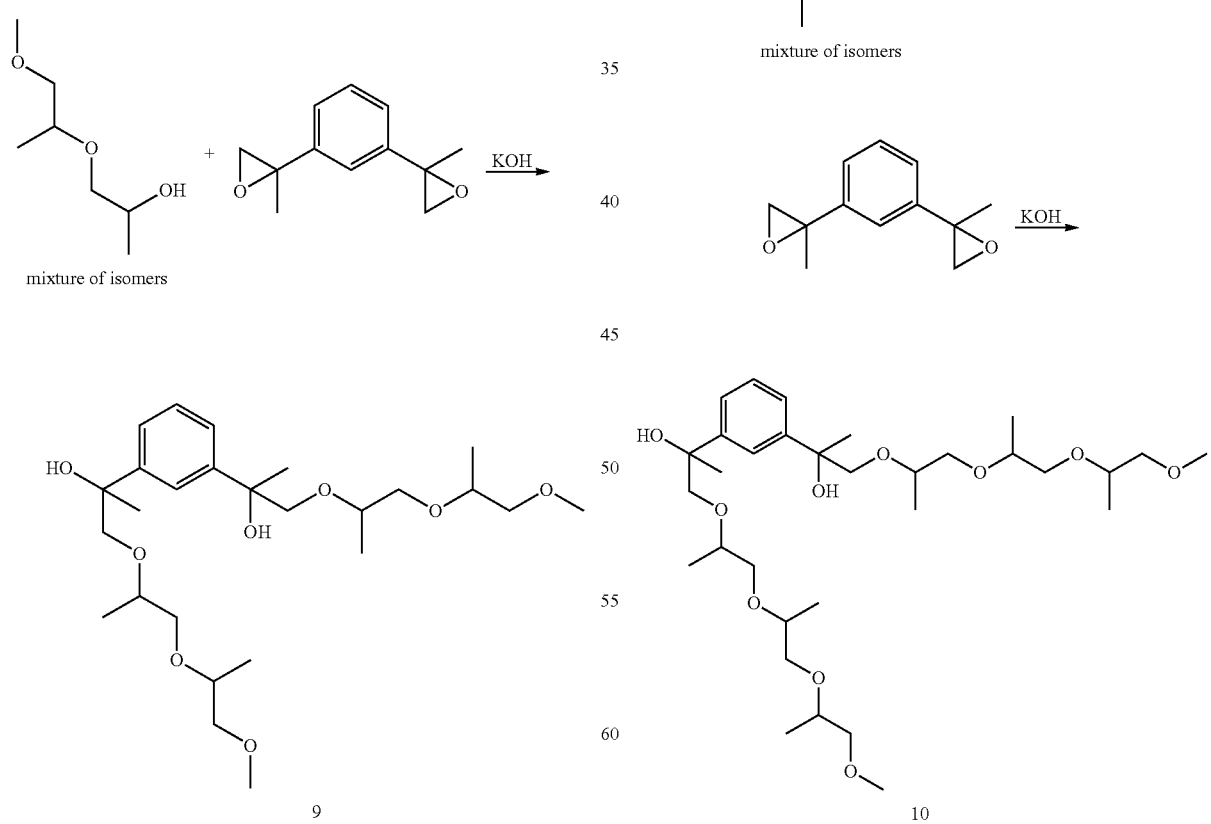

LC-MS $t_R$: 6.40 min (Exact mass: 486.32 m/z, found: 486.3 m/z).

LC-MS $t_R$: 7.41 min (Exact mass: 602.40 m/z, found: 602.4 m/z).

Example 11: Preparation of 2,2'-(1,3-phenylene)bis(1-(2-(2-methoxyethoxy)ethoxy)propan-2-ol) [11]

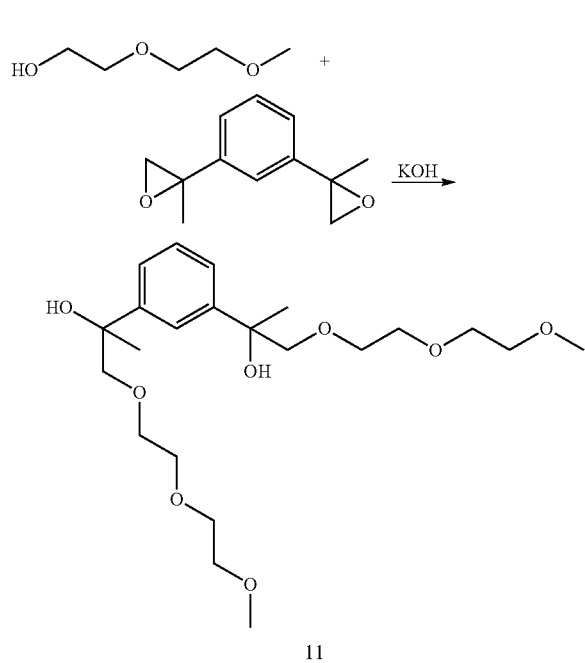

LC-MS $t_R$: 4.56 min (Exact mass: 430.26 m/z, found: 430.3 m/z).

Example 12: Preparation of 2,2'-(1,3-phenylene)bis(1-(2-(2-ethoxyethoxy)ethoxy)propan-2-ol) [12]

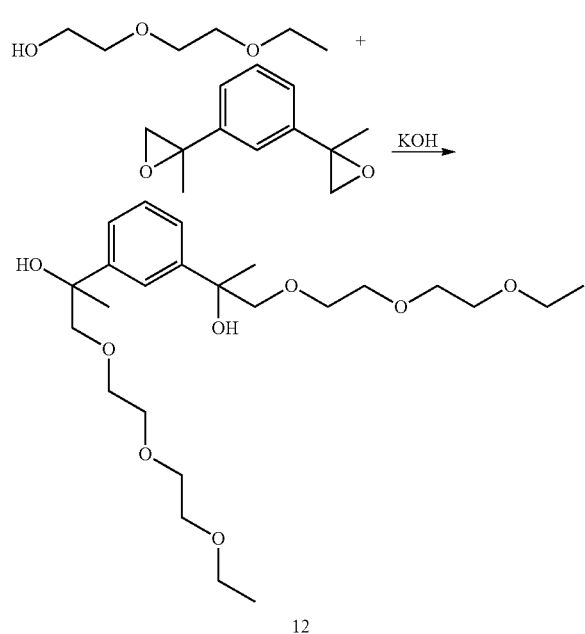

LC-MS $t_R$: 5.26 min (Exact mass: 458.29 m/z, found: 458.3 m/z).

Example 13: Preparation of 2,2'-(1,3-phenylene)bis(1-(2-(2-propoxyethoxy)ethoxy)propan-2-ol) [13]

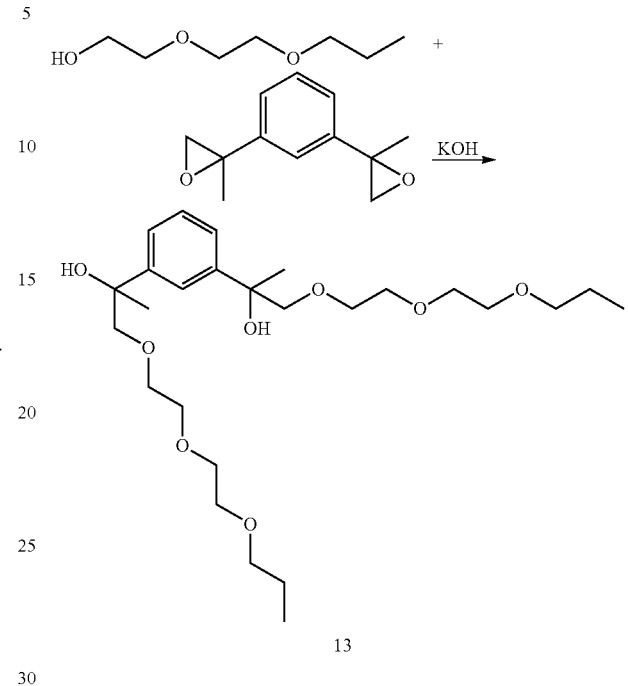

LC-MS $t_R$: 6.60 min (Exact mass: 486.32 m/z, found: 486.3 m/z).

Example 14: Preparation of 2,2'-(1,3-phenylene)bis(1-(2-(2-butoxyethoxy)ethoxy)propan-2-ol) [14]

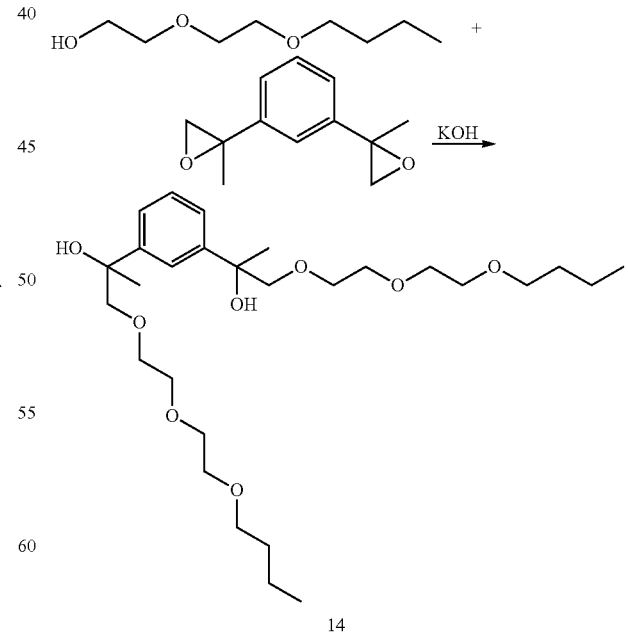

LC-MS $t_R$: 7.73 min (Exact mass: 514.35 m/z, found: 514.3 m/z).

Example 15: Preparation of 13,13'-(1,3-phenylene) bis(2,5,8,11-tetraoxatetradecan-13-ol) [15]

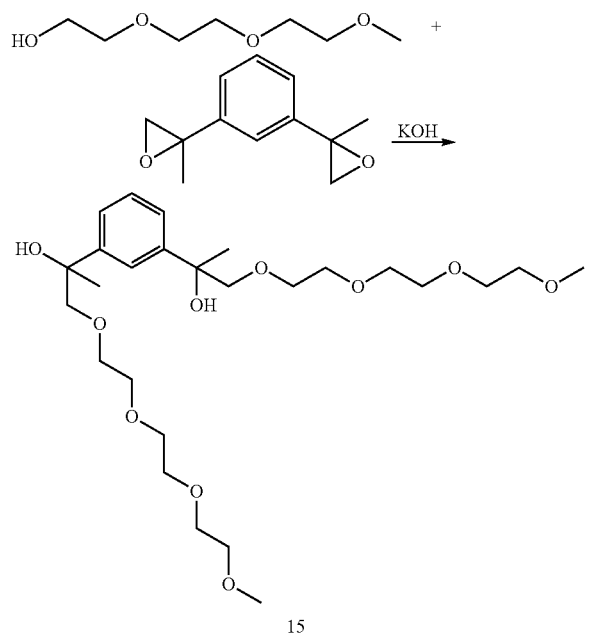

15

LC-MS $t_R$: 4.63 min (Exact mass: 518.31 m/z, found: 518.3 m/z).

Example 16: Preparation of 2,2'-(1,3-phenylene)bis (4,7,10,13-tetraoxaheptadecan-2-ol) [16]

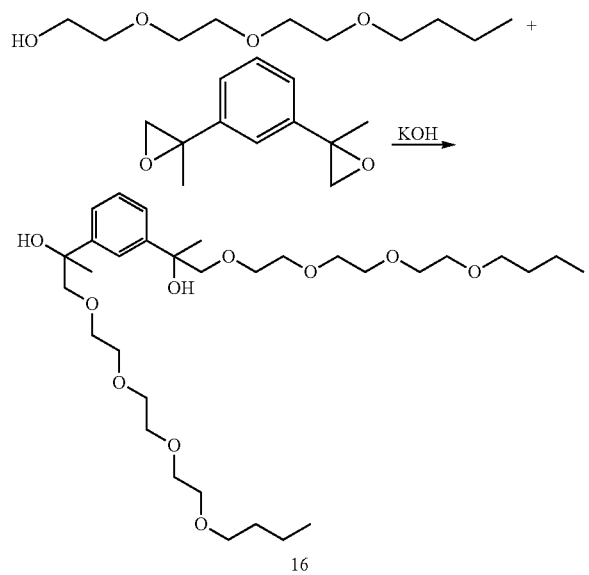

16

LC-MS $t_R$: 7.66 min (Exact mass: 602.40 m/z, found 602.4 m/z).

LC-MS Instrument Conditions (Agilent 1100 LC):
Sample Prep: 2-3 mg/mL in DMSO
Column: Zorbax XDB-C18×4.6 mm, 5 μm
Column Temp: 40° C.
Injection Volume: 24
DAD: 190-600 nm collection
Pump Conditions: Initial—97% water (2.5 mM NH$_4$OAc) (Solvent A) and 3% acetonitrile (Solvent B)
Gradient:

| Time (min) | % Solvent A | % Solvent B | Flow (mL/min) |
|---|---|---|---|
| 0 | 97 | 3 | 1.0 |
| 10 | 0 | 100 | 1.0 |
| 25 | 0 | 100 | 1.0 |
| 25.1 | 97 | 3 | 1.0 |
| 30 | 97 | 3 | 1.0 |

Mass spectra were acquired with a Micromass LCT mass spectrometer, which was coupled to the LC. Mass spectra were collected using electrospray ionization in both the positive-ion and negative ion modes. Ammonium acetate (50 mM in MeOH) was added post column (0.1 mL/min) to enhance ionization efficiency. ES+/ES− scane range was 60-3300 amu (25 and 75V).

The invention has been described in detail with reference to the embodiments disclosed herein, but it will be understood that variations and modifications can be effected within the spirit and scope of the invention.

I claim:

1. A compound according to Formula I:

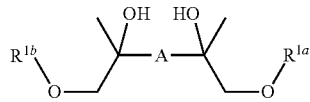

I wherein: A is ($C_{8-20}$) aryl;
$R^{1a}$ and $R^{1b}$ are independently

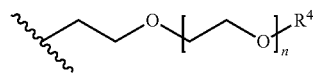

or

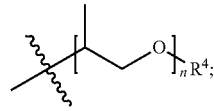

each $R^4$ is independently ($C_{1-12}$)alkyl, or —C(O)$R^5$;
each $R^5$ is ($C_{1-12}$)alkyl unsubstituted or substituted by $R^6$, ($C_{2-12}$)alkenyl unsubstituted or substituted by $R^6$, ($C_{3-8}$)cycloalkyl, or 5- to 9-membered aryl;
each $R^6$ is ($C_{1-4}$)alkoxy, or oxo; and
each n is independently an integer from 1 to 15.

2. The compound of claim 1 wherein A is 1,2-, 1,3-, or 1,4-disubstituted phenyl.

3. The compound of claim 1 wherein $R^4$ is hydrogen or ethyl.

4. The compound of claim 1 wherein, n is an integer from 1 to 4.

5. The compound of claim 1 wherein the composition has a volatile organic content of less than 50 wt % according to ASTM D6886.
6. An aromatic dicarbinol compound having Formulas 1-16:
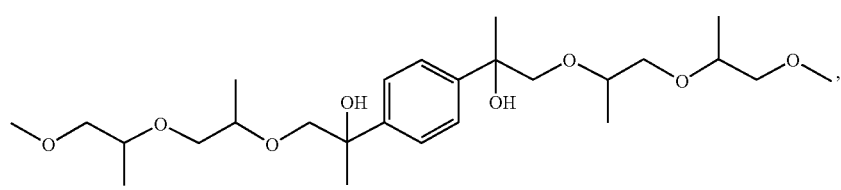
1
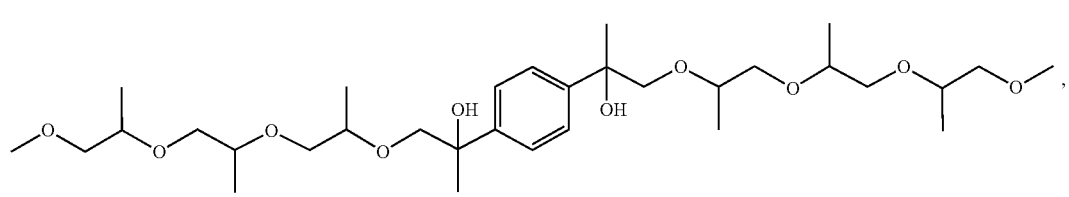
2
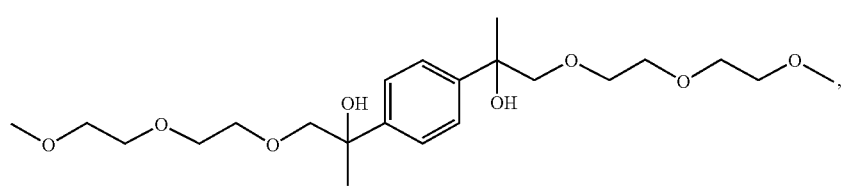
3
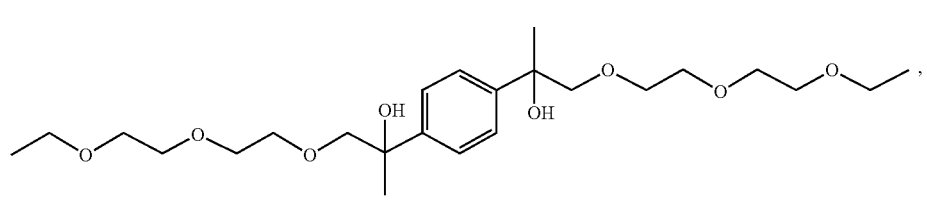
4
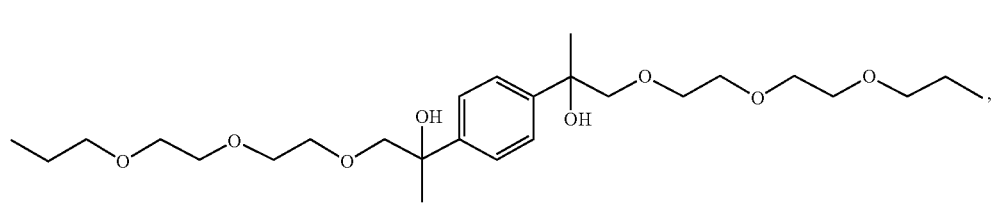
5
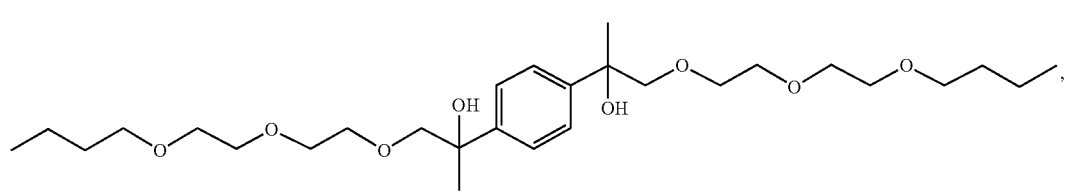
6
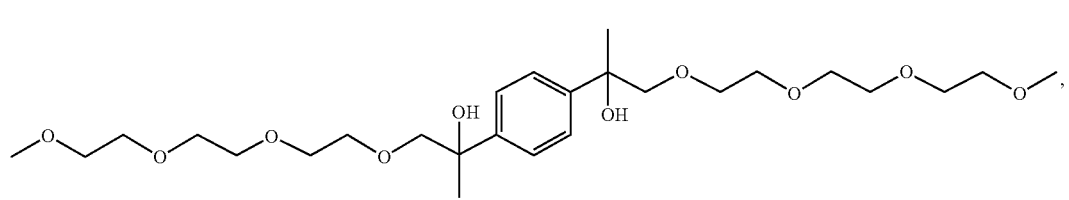
7

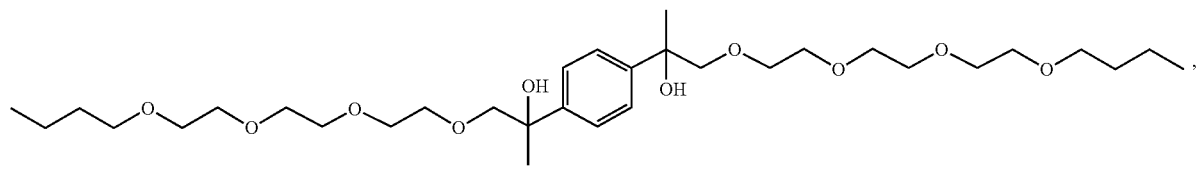
8
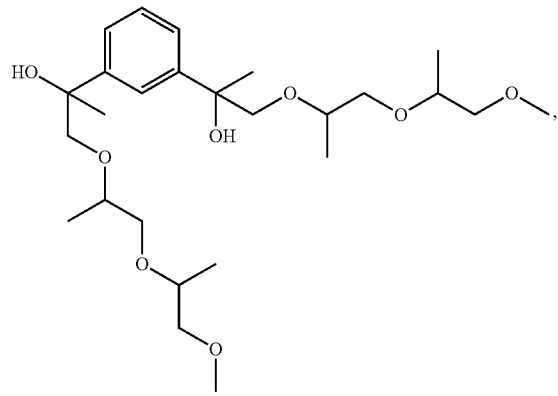
9
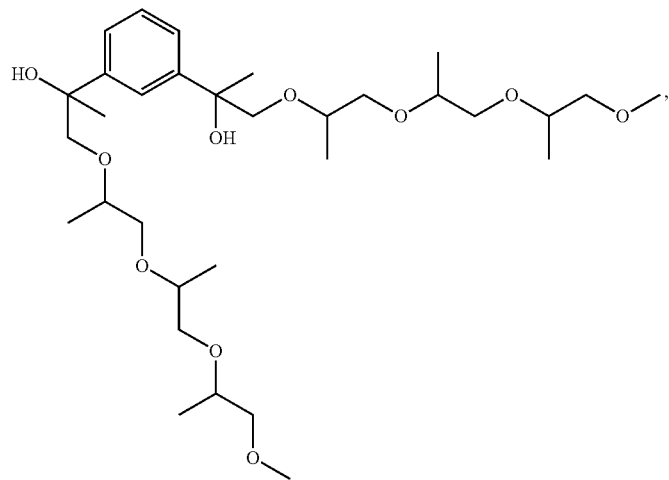
10
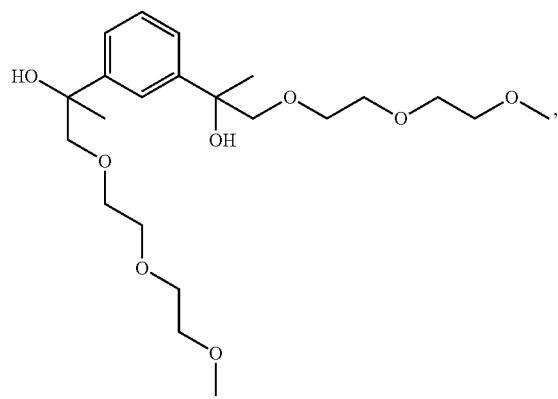
11
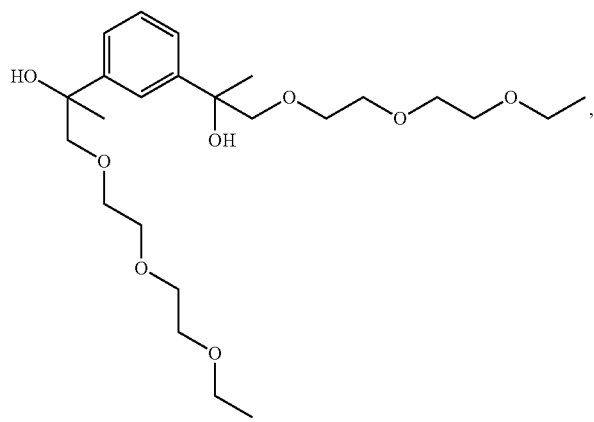
12

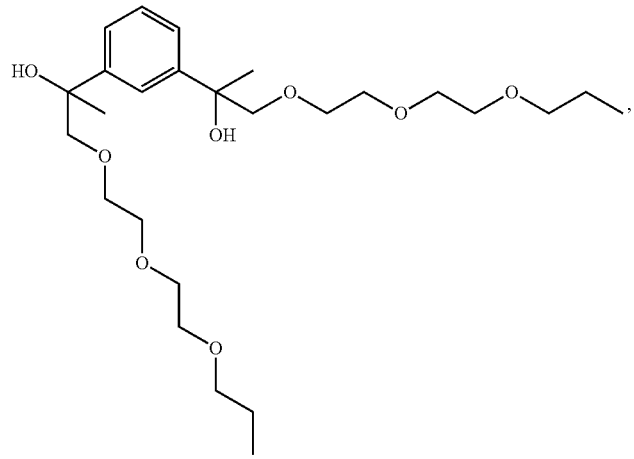
13
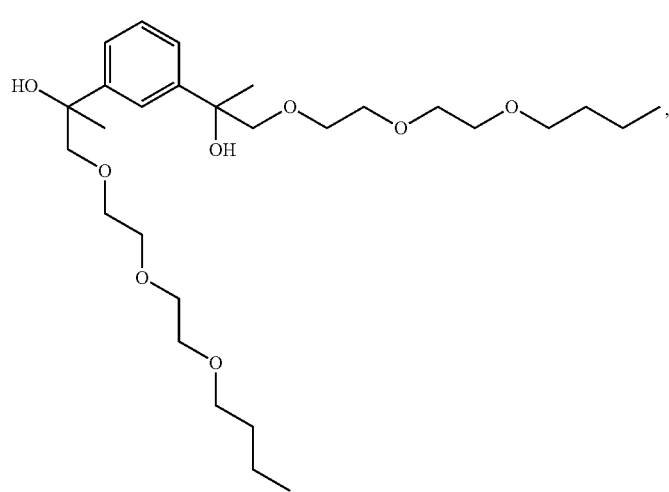
14
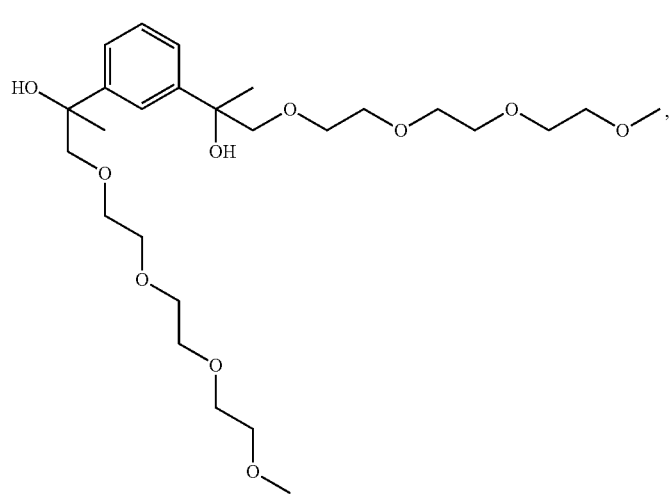
15

16
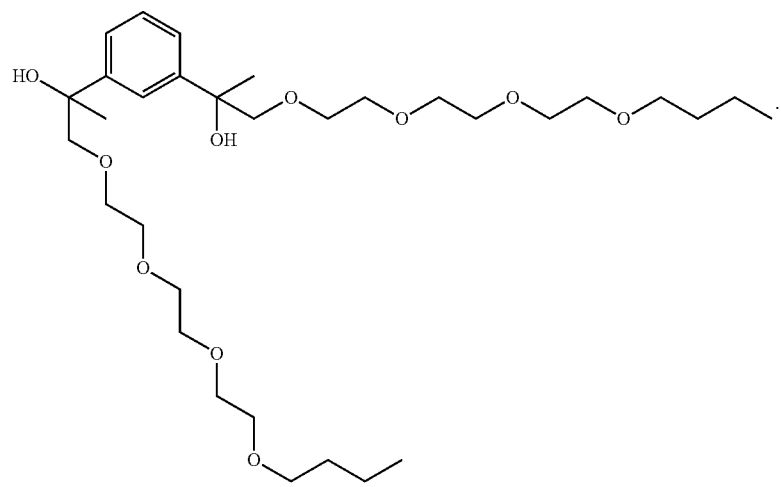
and isomers thereof.
* * * * *